United States Patent
Ardizzone et al.

(10) Patent No.: US 7,354,393 B2
(45) Date of Patent: Apr. 8, 2008

(54) MAGNETIC FOOT THERAPEUTIC APPARATUS AND METHOD

(76) Inventors: Vincent Ardizzone, P.O. Box 572, Port Jefferson, NY (US) 11777-0572; Thomas Bove, 17625 E. Euclid Ave., Spokane, WA (US) 99216-1737

( * ) Notice: Subject to any disclaimer, the term of this patent is extended or adjusted under 35 U.S.C. 154(b) by 750 days.

(21) Appl. No.: 10/720,616

(22) Filed: Nov. 24, 2003

(65) Prior Publication Data

US 2004/0106843 A1   Jun. 3, 2004

Related U.S. Application Data

(63) Continuation-in-part of application No. 10/318,552, filed on Dec. 13, 2002, which is a continuation-in-part of application No. 10/087,135, filed on Feb. 28, 2002, now Pat. No. 6,648,812.

(60) Provisional application No. 60/272,384, filed on Feb. 28, 2001.

(51) Int. Cl.
*A61N 2/06* (2006.01)

(52) U.S. Cl. .......................................................... 600/9

(58) Field of Classification Search ............. 600/9–15; 601/1, 15, 18, 19, 22, 27–32, 49, 50, 52, 601/54, 61, 63, 64, 110–113, 117–119, 122, 601/127–131

See application file for complete search history.

(56) References Cited

U.S. PATENT DOCUMENTS

| 435,376 | A | | 8/1890 | Brown | |
|---|---|---|---|---|---|
| 2,276,510 | A | | 3/1942 | Newton | 128/41 |
| 4,846,159 | A | * | 7/1989 | Anzai et al. | 601/128 |
| 5,096,188 | A | | 3/1992 | Shen | 272/96 |
| 5,152,281 | A | | 10/1992 | Koll | 128/57 |
| D363,556 | S | | 10/1995 | Katsunuma et al. | D24/213 |
| 5,632,720 | A | | 5/1997 | Kleitz | 601/15 |
| 5,868,688 | A | * | 2/1999 | Avidor et al. | 601/87 |
| 5,996,163 | A | * | 12/1999 | Galizia | 15/160 |
| 6,013,042 | A | | 1/2000 | Sakai | 601/134 |
| 6,065,210 | A | * | 5/2000 | Bove | 29/895.21 |
| 6,102,875 | A | | 8/2000 | Jones | 601/113 |
| D435,111 | S | | 12/2000 | Kuo | D24/213 |
| 6,405,390 | B2 | | 6/2002 | Kuen | 4/622 |
| 6,602,212 | B1 | * | 8/2003 | Ahn | 601/154 |
| 6,866,776 | B2 | * | 3/2005 | Leason et al. | 210/201 |
| 2002/0151760 | A1 | | 10/2002 | Paturu | 600/15 |
| 2003/0004443 | A1 | | 1/2003 | Chan | 601/22 |

FOREIGN PATENT DOCUMENTS

| EP | 0294513 | 12/1988 | |
|---|---|---|---|
| FR | 2789893 | 2/1999 | |
| NL | WO 94/27675 | 12/1994 | 2/2 |

* cited by examiner

*Primary Examiner*—Charles A Marmor, II
*Assistant Examiner*—Christine D Hopkins
(74) *Attorney, Agent, or Firm*—Cislo & Thomas, LLP

(57) ABSTRACT

Provided are exemplary embodiments of a magnetic therapy device, which may include a rotatable housing, a first magnetic element configured to rotationally couple to said rotatable housing, a second magnetic element adjacent to said rotatable housing that affects the rotation of said first magnetic element, such that said first magnetic element simultaneously rotates about two axes, and an enclosure configured to enclose the magnetic therapeutic device, and configured to receive a portion of a body for treatment.

17 Claims, 4 Drawing Sheets

MAGNETIC FOOT THERAPEUTIC APPARATUS AND METHOD

CROSS REFERENCE TO RELATED APPLICATIONS

This application is a continuation-in-part of U.S. patent application Ser. No. 10/318,552, filed Dec. 13, 2002, which claims the benefit of U.S. patent application Ser. No. 10/087,135, filed Feb. 28, 2002 now U.S. Pat. No. 6,648,812, which claims the benefit of U.S. Provisional Patent Application Ser. No. 60/272,384 filed Feb. 28, 2001. These applications are incorporated by reference as if fully stated herein.

BACKGROUND

Various devices may have been made to create time-varying magnetic fields for use on the human body. Generally, two types of time-varying magnetic fields may have been used. The first type may use an alternating current ("AC") field that is produced when electric current is caused to alternate at any given frequency. In accordance with Maxwell's equations, a magnetic field is concurrently produced at the same frequency as the electric field. Included in this first type of time-varying magnetic field device may be pulsed electromagnetic fields (PEMF) which are generated when a current is caused to move through a conductor in discrete impulses of electric charge moving in the same direction.

A second general type of device that may be used for creating time-varying magnetic fields involves physically moving a static magnetic field through space. While linear displacement may be one way to accomplish this, another common method may be rotating the static magnetic field.

The source of the static magnetic field may be generally a permanent magnet, since an electromagnet may require considerable expenditure of energy in the form of current generation and the subsequent dissipation of unwanted heat energy.

The therapeutic uses of time-varying magnetic fields may have been described and clinically evaluated in numerous literatures. The more popular publications written for the general public may include "Magnetic Therapy" by Dr. Ronald Lawrence and Dr. Paul Rosch, "The Pain Relief Breakthrough" by Dr. Julian Whitaker and Brenda Adderly, and "Magnetic Therapy in Eastern Europe" by Dr. Jiri Jerabek and Dr. William Pawluk. These books may offer numerous references to clinical studies which purport to show the effectiveness of time-varying magnetic fields for the treatment of a multitude of chronic and acute conditions including atherosclerosis, carpal tunnel syndrome, chronic bronchitis, post-ischemic injury, edema, fractures, infected wounds, limb grafts, burns, scars, macular degeneration, etc. The lack of any substantial negative side effects is also purported for most treatments. In recent years, the general public and even the medical community may have increasingly accepted magnetic therapy as an alternative treatment worthy of consideration for such conditions.

When people suffer from pain, they may usually ingest analgesics from their doctors. Some of them may also seek help from physical therapists to relieve their pain, if it is musculo-skeletal in nature. Furthermore, many people may be willing to purchase all sorts of pain-relieving devices that may be available on the market as home remedies. The most common devices may be products in which pressure is applied to the soles of the feet, such as massage shoes and insoles.

It may have been known for some time that electrical activity in some form is involved in many aspects of human physiology. For instance, electrical activity may have been measured during the regeneration of bone. In addition, it may be well documented that many cellular responses are dictated by electrical gradients generated in the cell (for example, nerve cells). Therefore, it may be possible that exposure of the human body to a pulsating electromagnetic field could produce a beneficial physiological response in the body. In fact, several studies may have shown beneficial effects of pulsating electromagnetic field therapy.

Foot massage devices may have been sold on the market for years. Most may provide stimulation to the feet via mechanical vibration of surface plates that contact the feet. Other devices may provide a bath basin such that the feet may soak in a solution while the device produces heat and vibration to simultaneously or separately stimulate the feet. Furthermore, magnetic pads may have been used and marketed for years. These devices may rely on static magnetic fields to produce therapeutic effects.

Dynamic magnetic fields may have enhanced therapeutic effects. However, dynamic fields that may be currently utilized may be generated by electromagnetic devices that produce pulsed electromagnetic fields (PEMF), or alternating current (AC) electromagnetic fields. These types of dynamic electromagnetic fields may not provide the same characteristics of dynamic electromagnetic fields produced by rotating permanent magnets. The magnetic flux lines created by PEMF or AC electromagnetic fields may vary in density and intensity in a time varying cyclical manner. Furthermore, the path of the flux lines may not change unless the device is manually positioned at different angles with respect to the treatment area. Rotating permanent magnets may produce dynamic electromagnetic fields that continually change in flux density and flux path. Additionally, if the permanent magnets rotate in two axes simultaneously, an added dimension of flux density may be created.

It may be advantageous to provide a therapeutic foot device that may utilize dynamic magnetic fields created by rotating permanent magnets. Furthermore, it may be advantageous to provide more and varied paths of flux movement to a treatment area.

SUMMARY

Exemplary embodiments disclosed herein are directed to a magnetic therapy device, which may include a rotatable housing, a first magnetic element configured to rotationally couple to said rotatable housing, a second magnetic element adjacent to said rotatable housing that affects the rotation of said first magnetic element, such that said first magnetic element simultaneously rotates about two axes, and an enclosure configured to enclose the magnetic therapeutic device, and configured to receive a portion of a body for treatment.

DETAILED DESCRIPTION

The detailed description set forth below in connection with the appended drawings is intended as a description of exemplary embodiments and is not intended to represent the only forms in which the embodiments may be constructed and/or utilized. The description also sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
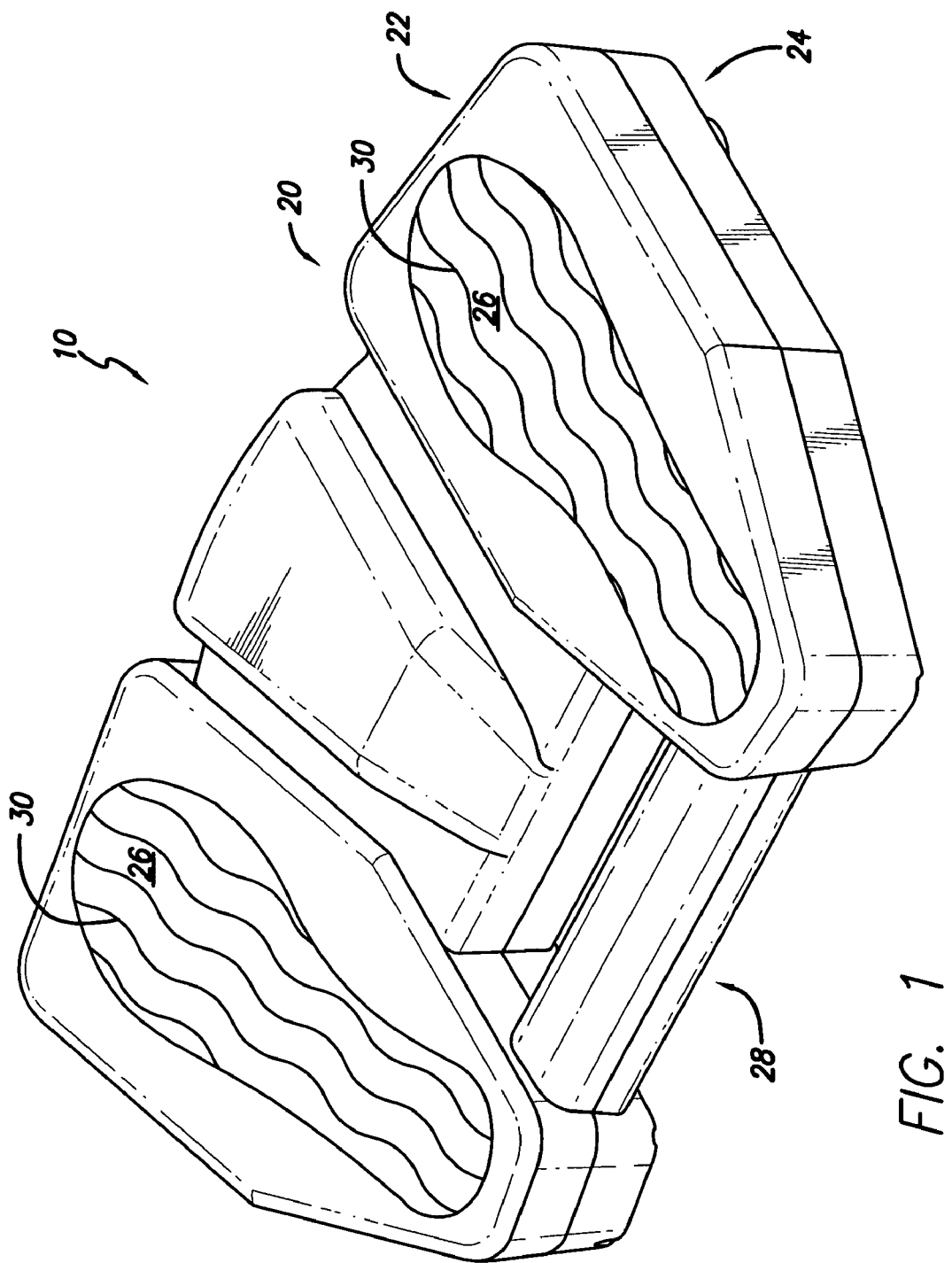
FIG. 1 is a perspective view of an exemplary embodiment of a foot energizer system.

A foot energizer system is shown in FIG. 1, generally at 10. System 10 includes an enclosure 20, which may be include an upper portion 22 and a lower portion 24. Upper portion 22 may have body access areas, or therapy area 26 configured to allow a user to position a body part adjacent the system for treatment. Furthermore, system 10 may be configured with a handle configuration 28 that would allow easy transport of the entire system.

Enclosure 20 may be made of a hard plastic or metal, but may be made of other materials, as desired. Upper portion 22 may be configured to couple to lower portion 24 to form the enclosure 20. Upper portion 22 and lower portion 24 may be coupled via screws, bolts, rivets, a snap configuration, or other coupling configurations, as desired.

Body access areas 26 may include heat elements 30 configured to transfer heat to the user's body while using the system. In this manner, heat may be transferred to soothe and comfort a user's body, as desired. Body access areas 26 may be made of a soft rubber, with an irregular surface such that if the system 10 or body access areas 26 vibrate, it would provide massage-like motion for the treatment area. Furthermore body access areas may be generally horizontal to allow a foot of a user to be adjacent thereto. With this configuration, a user may place their feet upon the device to receive treatment from the device.

Figure 2:
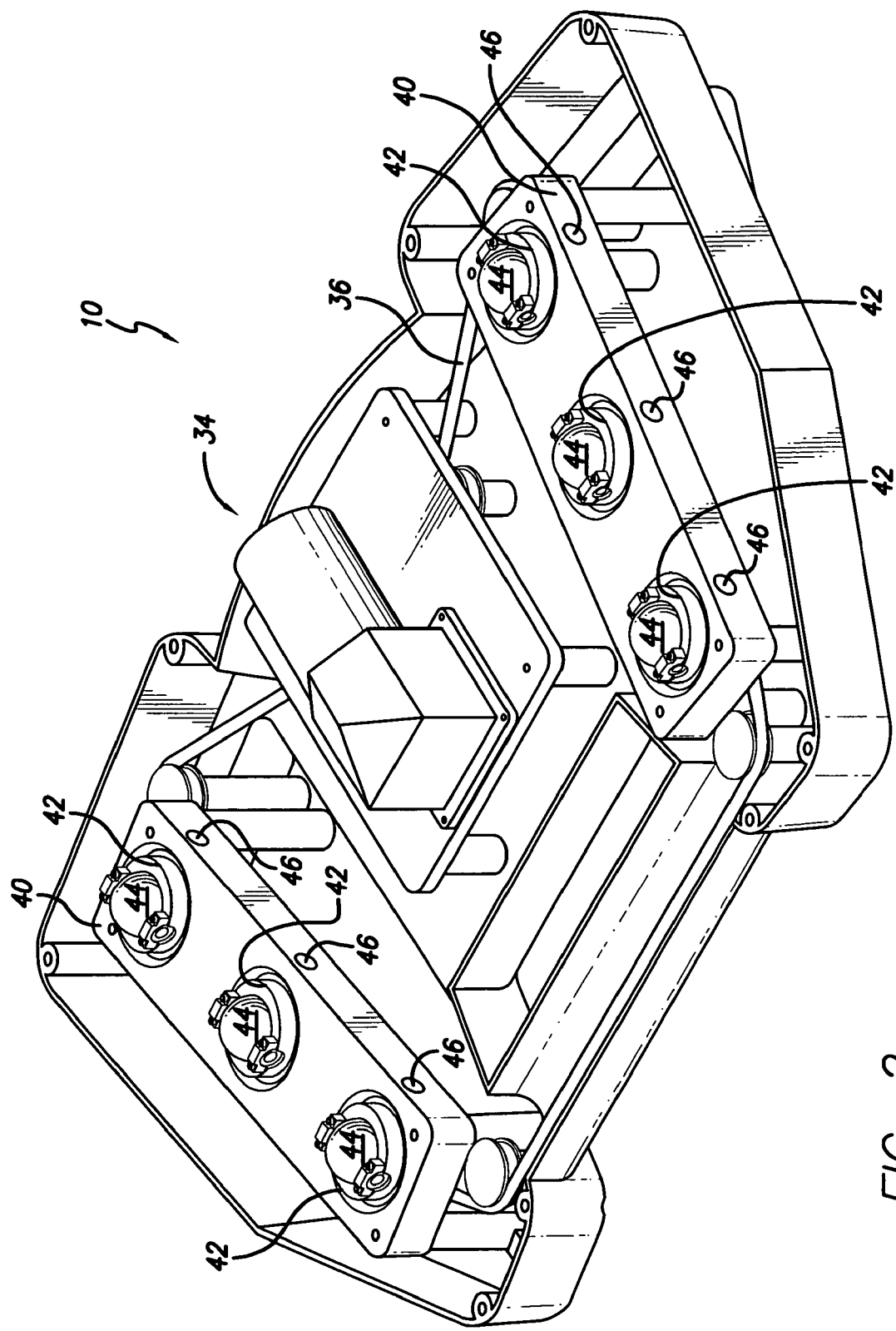
FIG. 2 is a perspective view of an exemplary embodiment of the interior of a foot energizer system.

FIG. 2 shows the portions of the system 10 that may reside inside enclosure 20. System 10 further may include a force system including a motor assembly 34 that may provide rotational force for the entire system. System 10 may also include a belt 36 that may be rotationally coupled to the motor assembly 34 such that the belt may move when the motor assembly is activated. System 10 may also include one or more casings 40 that may be configured to couple to rotatable housings 42.

Rotatable housings 42 may be able to couple to a first magnetic element 44 such that the first magnetic element may rotate within rotatable housing 42. System 10 may also further include a second magnetic element 46 that may be adjacent casing 40 and/or rotatable housing 42, such that it may affect the rotation of rotatable housing 42 and/or first magnetic element 44.

Rotatable housing 42 may be configured to rotationally couple to belt 36 such that when the motor assembly 34 is activated, belt 36 may move, rotatable housing 42 may then rotate within casing 40, thus causing first magnetic element 44 to rotate about a vertical axis. Furthermore, second magnetic element 46 may cause first magnetic element 44 to rotate in a horizontal axis that may be somewhat perpendicular to the first axis of rotation. In this manner, first magnetic element 44 may rotate in two or more axes simultaneously.

Motor assembly 34 may include a motor gearing, pulleys and other devices such that it may transfer motion to belt 36, however, other configurations may be utilized, as desired.

Belt 36 may be made from a rubber or nylon material, but also may be a chain or drive-belt, or other device that may translate rotational motion to the rotatable housings, as desired.

Casing 40 may be made from a milled aluminum or other metal, but may be made from other materials such as, but not limited to, hard plastic or other material. Casing 40 may be mounted to the lower portion 24 of enclosure 20 via screws or bolts and stanchions, however other fastening methods may be utilized, as desired.

Rotatable housing 42 may be made of a milled aluminum or metal material, but other materials may be utilized, as desired. Rotatable housing 42 is configured to rotatably couple to casing 40. This may be accomplished via bearings or other type of rotatable coupling, as desired. First magnetic element 44 may include an axle that extends through first magnetic element 44 and may then be secured on either side of first magnetic element 44 within rotatable housing 42. The axle may be secured to rotatable housing 42 via a bearing, or other rotatable coupling method.

It will be appreciated that although first magnetic element 44 is shown as being coupled to rotatable housing 42 via machine screws and bearings, other coupling configurations may be utilized, such as, but not limited to, bolts, adhesives, rivets, nails, clamps and orifices being configured directly in casing 40. Additionally, first magnetic element 44 may be coupled to rotatable housing 42 via bearings that fit into an orifice formed within rotatable housing 42.

Figure 3:
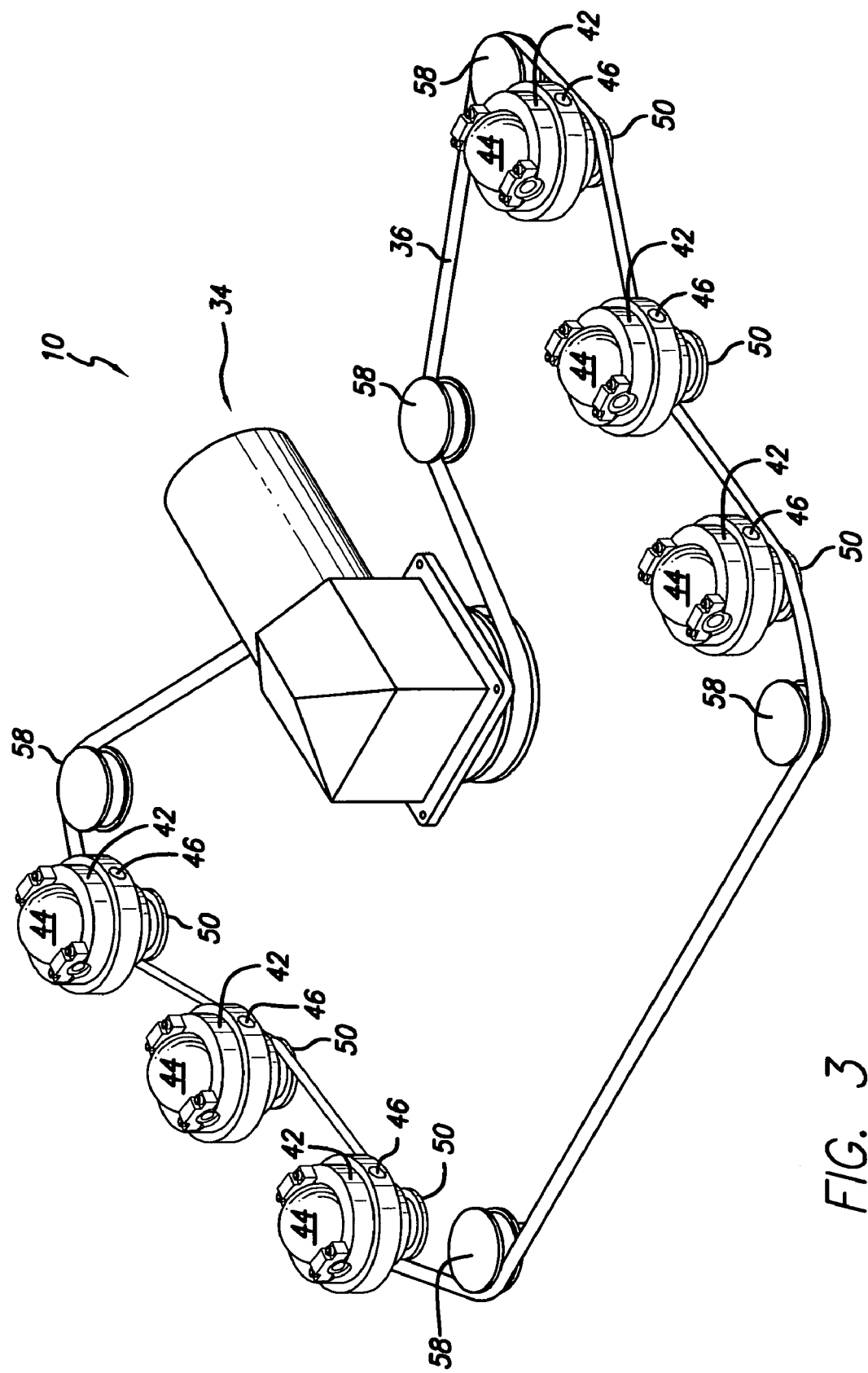
FIG. 3 is a perspective view of an exemplary embodiment of the mechanical force configuration of a foot energizer system.

FIG. 3 may show an exemplary embodiment of the system 10 without the enclosure. Again, the system may include a motor assembly 34, belt 36 and rotatable housings 42. The system may also include other pulleys 58 that would provide tensioning of belt 36 and/or other functions for the system. Again, the system may include a first magnetic element 44 that may rotate within rotatable housing 42 such that when the motor is activated, it may translate rotational motion to belt 36, then belt 36 may provide rotational motion to the rotatable housings 42 via pulleys 50 such that rotatable housing 42 may rotate, as may first magnetic element 44, which may be caused by the translated force of the motor assembly and belt.

Furthermore, a second force, namely the magnetic force of second magnetic elements 46, may provide rotation for first magnetic element 44 in another axis such that when the system is operational, first magnetic element 44 will rotate in more than one axis, simultaneously. First magnetic element 44 may be a permanent magnet, but may be other types of magnetic element, such as, but not limited to an electrically magnetized element. Similarly, second magnetic element 46 may also be a permanent magnet, but may be another type of magnetic element, as desired.

Figure 4:
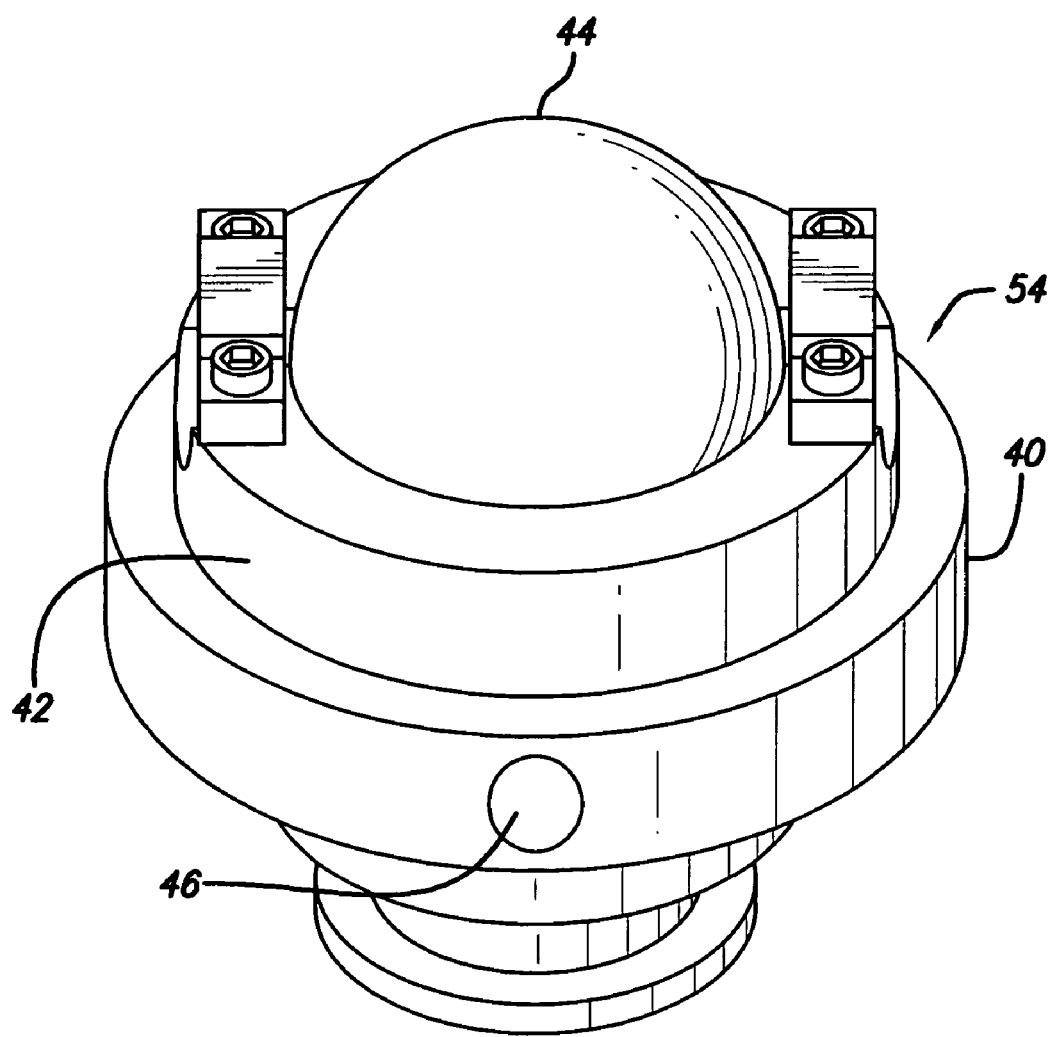
FIG. 4 is a perspective view of an exemplary embodiment of a magnetic biaxial rotating system.

FIG. 4 shows a close-up of a rotational housing 42 and first magnetic element 44 according to an exemplary embodiment. A portion of casing 40 may also be shown around rotatable housing 42 with second magnetic element 46 also being shown. It will be appreciated that although second magnetic elements 46 are shown at opposite sides of casing 40, they may be positioned in any position adjacent rotatable housing 42 to affect the rotation of rotatable housing 42 and first magnetic element 44, as desired. This placement may be within rotatable housing 42, casing 40 or other configuration to affect first magnetic element 44.

First magnetic element 44 may have an axle 54 that extends through first magnetic element 44 such that the ends of axle 54 may couple to rotatable housing 42 to allow rotation of first magnetic element 44 with respect to rotatable housing 42 and casing 40. Axle 54 may be rotationally coupled to rotatable housing 42 via bearings, however it will be appreciated that other rotational coupling configurations may be utilized, as desired.

When the system is activated, the rotatable housings 42 and first magnetic element 44 may rotate, which may cause a vibration that may provide massage-like effects to the treatment area, including body parts, and may vibrate the enclosure. With this configuration, magnetic therapy, as well as vibrational and heat therapy, may be applied to a treatment including, but not limited to, a user's feet or other body part, with this system. Motor assembly 34 may be powered by batteries, an A/C plug, or other methods, as desired. It will be appreciated that although two casings have been shown, each with three rotatable housings and three corresponding first magnetic elements, other configurations, including other numbers and configurations of these portions, may be utilized, as desired.

In closing, it is to be understood that the exemplary embodiments described herein are illustrative of the principles of the present invention. Other modifications that may be employed are within the scope of the invention. Thus, by way of example, but not of limitation, alternative configurations may be utilized in accordance with the teachings herein. Accordingly, the drawings and description are illustrative and not meant to be a limitation thereof. Thus, it is intended that the invention cover all embodiments and variations thereof as long as such embodiments and variations come within the scope of the appended claims and their equivalents.

What is claimed is:

1. A magnetic foot therapeutic apparatus, comprising:
   at least one foot therapy area;
   a plurality of magnetic members disposed substantially under said at least one foot therapy area and adapted to revolve simultaneously about two axes to provide magnetic therapy to a user's foot placed over said at least one foot therapy area;
   an enclosure for said magnetic members;
   said enclosure houses at least one magnetic member casing;
   said at least one foot therapy area is formed on an exterior surface of said enclosure;
   said at least one magnetic member casing is adapted to rotatably accommodate a plurality of magnetic member housing units;
   each of said housing units is adapted to revolve about a first axis of rotation; and
   each of said magnetic members has a respective housing unit and is adapted to revolve about a second axis of rotation within a respective housing unit, while said housing unit revolves about said first axis of rotation.

2. The magnetic foot therapeutic apparatus of claim 1, wherein said at least one foot therapy area is adapted to provide heat therapy to a user's foot placed over said at least one foot therapy area.

3. The magnetic foot therapeutic apparatus of claim 1, wherein each of said magnetic members simultaneously revolves about said first and second axes to provide magnetic therapy to a user's foot placed over said at least one foot therapy area.

4. The magnetic foot therapeutic apparatus of claim 3, wherein each of said housing units is equipped with a pair of oppositely disposed permanent magnets, said oppositely disposed permanent magnets being operatively coupled to a respective magnetic member.

5. The magnetic foot therapeutic apparatus of claim 4, wherein said pair of oppositely disposed permanent magnets cause said respective magnetic member to revolve about said second axis of rotation within said housing unit while said housing unit revolves about said first axis of rotation.

6. The magnetic foot therapeutic apparatus of claim 5, wherein each of said magnetic members has a substantially spherical configuration.

7. The magnetic foot therapeutic apparatus of claim 6, wherein each of said magnetic members is made from permanent magnet material.

8. The magnetic foot therapeutic apparatus of claim 7, wherein each of said housing units has a substantially ring-shaped configuration.

9. The magnetic foot therapeutic apparatus of claim 8, wherein each of said magnetic members is adapted to revolve on a central axle within a respective substantially ring-shaped housing unit, said central axle having a longitudinal axis.

10. The magnetic foot therapeutic apparatus of claim 9, wherein each end of said central axle is securely engaged with of said substantially ring-shaped housing unit.

11. The magnetic foot therapeutic apparatus of claim 10, wherein said longitudinal axis of said central axle defines said second axis of rotation.

12. The magnetic foot therapeutic apparatus of claim 11, further comprising means for simultaneously revolving each of said housing units about said first axis of rotation.

13. The magnetic foot therapeutic apparatus of claim 12, wherein said simultaneous revolving means includes at least one motor operatively coupled to a shaft on each of said housing units via a belt and a plurality of pulleys.

14. The magnetic foot therapeutic apparatus of claim 13, wherein each shaft has a longitudinal axis.

15. The magnetic foot therapeutic apparatus of claim 14, wherein said longitudinal shaft axis defines said first axis of rotation.

16. The magnetic foot therapeutic apparatus of claim 15, wherein said belt is adapted to operate under said at least one casing.

17. The magnetic foot therapeutic apparatus of claim 1, wherein said at least one foot therapy area has an irregular surface configured to provide massage-like treatment to a user's foot placed over said at least one foot therapy area.

* * * * *